US010850045B2

(12) United States Patent
Kodama et al.

(10) Patent No.: US 10,850,045 B2
(45) Date of Patent: Dec. 1, 2020

(54) PUNCTURE INJECTION INSTRUMENT

(71) Applicant: TOPPAN PRINTING CO., LTD., Taito-ku (JP)

(72) Inventors: Yoshihiro Kodama, Taito-ku (JP); Tomoya Sumida, Taito-ku (JP)

(73) Assignee: TOPPAN PRINTING CO., LTD., Taito-ku (JP)

( * ) Notice: Subject to any disclaimer, the term of this patent is extended or adjusted under 35 U.S.C. 154(b) by 622 days.

(21) Appl. No.: 15/283,563

(22) Filed: Oct. 3, 2016

(65) Prior Publication Data

US 2017/0021112 A1   Jan. 26, 2017

Related U.S. Application Data

(63) Continuation of application No. PCT/JP2015/001863, filed on Mar. 31, 2015.

(30) Foreign Application Priority Data

Apr. 3, 2014   (JP) .................................. 2014-077293
Nov. 12, 2014   (JP) .................................. 2014-229631

(51) Int. Cl.
*A61M 5/32*   (2006.01)
*A61B 8/08*   (2006.01)
(Continued)

(52) U.S. Cl.
CPC ......... *A61M 5/3295* (2013.01); *A61B 5/0066* (2013.01); *A61B 5/441* (2013.01);
(Continued)

(58) Field of Classification Search
CPC ............ A61M 5/3295; A61M 5/31581; A61M 5/3158; A61M 2005/31588; A61M 5/46;
(Continued)

(56) References Cited

U.S. PATENT DOCUMENTS 6,659,949 B1 * 12/2003 Lang .................... A61B 8/0858
  600/438
7,645,238 B2 *  1/2010 Hirsh ...................... A61B 8/42
  600/464

(Continued)

FOREIGN PATENT DOCUMENTS

JP   2005-021677 A   1/2005
JP   2009-516572 A   4/2009
(Continued)

OTHER PUBLICATIONS

International Search Report dated Jun. 23, 2015, in PCT/JP2015/001863 filed Mar. 31, 2015.
(Continued)

*Primary Examiner* — Sanjay Cattungal
(74) *Attorney, Agent, or Firm* — Oblon, McClelland, Maier & Neustadt, L.L.P.

(57) ABSTRACT

A puncture injection instrument including a hollow needle body including a substrate having a first surface and a second surface opposite to the first surface, the hollow needle body having one or more projections which are formed on the first surface and each have a through hole penetrating from a distal end of the projection to the second surface of the substrate, and one or more probes positioned outside a region where the one or more projections are formed. The one or more probes include an ultrasound probe or an optical coherence tomography probe.

20 Claims, 7 Drawing Sheets

(51) Int. Cl.
*A61B 5/00* (2006.01)
*A61M 5/46* (2006.01)
*A61B 8/00* (2006.01)
*A61M 5/315* (2006.01)
*A61M 37/00* (2006.01)

(52) U.S. Cl.
CPC .......... *A61B 8/0858* (2013.01); *A61B 8/4444* (2013.01); *A61B 8/4477* (2013.01); *A61B 8/461* (2013.01); *A61M 5/3158* (2013.01); *A61M 5/31581* (2013.01); *A61M 5/46* (2013.01); *A61M 2005/31588* (2013.01); *A61M 2037/0061* (2013.01)

(58) Field of Classification Search
CPC ........... A61M 2037/0061; A61B 8/461; A61B 8/4477; A61B 8/4444; A61B 5/0066; A61B 8/0858; A61B 5/441
USPC .................................................. 600/437–480
See application file for complete search history.

(56) References Cited

U.S. PATENT DOCUMENTS

| | | | |
|---|---|---|---|
| 7,842,008 B2 | 11/2010 | Clarke et al. | |
| 7,904,138 B2 | 3/2011 | Goldman et al. | |
| 7,931,594 B2* | 4/2011 | Hirsh | A61B 8/12 600/454 |
| 7,983,738 B2 | 7/2011 | Goldman et al. | |
| 7,983,860 B2 | 7/2011 | Schuette | |
| 8,073,531 B2 | 12/2011 | Goldman et al. | |
| 8,150,500 B2 | 4/2012 | Goldman et al. | |
| 8,244,333 B2 | 8/2012 | Wood et al. | |
| 8,255,040 B2 | 8/2012 | Goldman et al. | |
| 8,295,904 B2 | 10/2012 | Goldman et al. | |
| 8,380,291 B2 | 2/2013 | Wood et al. | |
| 8,419,684 B2 | 4/2013 | Clarke et al. | |
| 2007/0055179 A1* | 3/2007 | Deem | A61M 37/0092 601/2 |
| 2008/0014627 A1* | 1/2008 | Merchant | A61M 37/0092 435/259 |
| 2008/0195036 A1* | 8/2008 | Merchant | A61N 7/00 604/24 |
| 2008/0197517 A1* | 8/2008 | Merchant | A61N 7/00 261/77 |
| 2008/0200863 A1* | 8/2008 | Chomas | A61P 17/00 604/22 |
| 2008/0200864 A1* | 8/2008 | Holzbaur | A61N 7/00 604/24 |
| 2008/0221519 A1 | 9/2008 | Schwach et al. | |
| 2009/0192493 A1 | 7/2009 | Meng et al. | |
| 2010/0247513 A1* | 9/2010 | Agee | A61K 31/56 424/94.67 |
| 2011/0257561 A1* | 10/2011 | Gertner | A61B 5/4893 601/2 |
| 2012/0065494 A1* | 3/2012 | Gertner | A61B 5/489 600/411 |
| 2013/0123629 A1* | 5/2013 | Rosenberg | A61B 8/429 600/442 |
| 2013/0197427 A1* | 8/2013 | Merchant | A61M 5/165 604/24 |
| 2013/0218129 A1 | 8/2013 | Clarke et al. | |
| 2014/0074076 A1* | 3/2014 | Gertner | A61B 6/12 606/12 |
| 2014/0193394 A1 | 7/2014 | Agee et al. | |
| 2014/0290666 A1 | 10/2014 | Agee et al. | |
| 2014/0336487 A1* | 11/2014 | Wang | A61B 5/150984 600/352 |
| 2016/0051224 A1* | 2/2016 | Striano | A61B 8/4455 600/461 |

FOREIGN PATENT DOCUMENTS

| | | |
|---|---|---|
| JP | 2009-523038 A | 6/2009 |
| JP | 2013-172847 A | 9/2013 |
| JP | 2013-226427 A | 11/2013 |
| JP | 2014-28145 A | 2/2014 |
| WO | WO 2006/131881 A1 | 12/2006 |
| WO | WO 2010/111525 A2 | 9/2010 |

OTHER PUBLICATIONS

Extended European Search Report dated Nov. 22, 2017 in Patent Application No. 15774122.4, citing documents AA-AD and AO-AP therein, 7 pages.

* cited by examiner

PUNCTURE INJECTION INSTRUMENT

CROSS-REFERENCE TO RELATED APPLICATIONS

The present application is a continuation of International Application No. PCT/JP2015/001863, filed Mar. 31, 2015, which is based upon and claims the benefits of priority to Japanese Application No. 2014-077293, filed Apr. 3, 2014 and Japanese Application No. 2014-229631, filed Nov. 12, 2014. The entire contents of these applications are incorporated herein by reference.

BACKGROUND OF THE INVENTION

Field of the Invention

The present invention relates to a puncture injecting instrument that makes a puncture with a projection having a hollow needle structure.

Discussion of the Background

Administration of a medicine such as a vaccine into a living body performed by an injection has been widely established. Although injections are a highly safe administration method, the injection is accompanied by a strong pain since injection needles puncture a living body deeply (subcutaneously). Especially in developing countries, infection and needle piercing accidents caused by reuse of injection needles constantly occur.

In this regard, as a medicine administration method that is an alternative to an injection, attention is being paid to a method of administering a medicine into skin by puncturing the skin using a needle body including a large number of micron-order projections as described in Patent Literature 1. According to this method, the length of the needle body is set to such a length that the needle body does not reach nerve cells in a dermic layer, whereby a painful sensation can be almost completely prevented at the time of the puncture into the skin.

Furthermore, when a vaccine is intradermally administered using the needle body, the vaccine is administered into the skin where there is an abundance of antigen-presenting cells. Therefore, the amount of vaccine to be used may be reduced compared with a subcutaneous injection.

A shape of the needle body needs to be sufficiently thin and have a distal end angle suitable for puncturing the skin, and a length sufficient for causing a medicine to permeate into the skin. Therefore, it is considered to be desirable that the needle body has a diameter of several tens μm to several hundred μm and has such a length that the needle body penetrates a cornified layer, i.e., the outermost layer of the skin, but does not reach a neural layer, and specifically has a length of about several hundred μm to several mm.

Patent Literature 1: JP-A-2005-021677
Patent Literature 2: JP-A-2009-516572

SUMMARY OF THE INVENTION

According to one aspect of the present invention, a puncture injection instrument includes a hollow needle body including a substrate having a first surface and a second surface opposite to the first surface, the hollow needle body having one or more projections which are formed on the first surface and each have a through hole penetrating from a distal end of the projection to the second surface of the substrate, and one or more probes positioned outside a region where the one or more projections are formed. The one or more probes include an ultrasound probe or an optical coherence tomography probe.

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawings, wherein.

DESCRIPTION OF THE EMBODIMENTS

The embodiments will now be described with reference to the accompanying drawings, wherein like reference numerals designate corresponding or identical elements throughout the various drawings.

A first embodiment of the present invention will be described with reference to the drawings.

(Hollow Needle Body)

Figure 1:
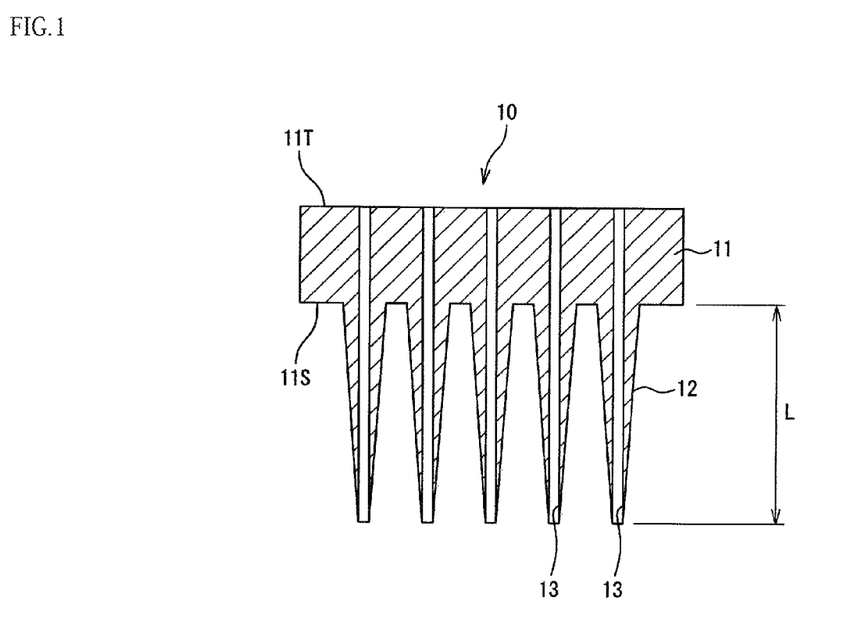
FIG. 1 is a schematic cross-sectional view illustrating a hollow needle body according to a first embodiment of the present invention.

As illustrated in FIG. 1, a hollow needle body 10 constituting a puncture injection instrument according to the first embodiment includes a disk-like substrate 11 and a plurality of projections 12 formed on a first surface 11S of the substrate 11. Each of the projections 12 is formed with a through hole 13 penetrating from a distal end side of the projection 12 to a second surface 11T of the substrate 11 opposite to the first surface 11S. The through hole 13 serves as a path for a medicine injection and guides a medicine from the second surface 11T to a distal end of the projection 12 on the first surface 11S.

FIG. 1 illustrates the case where the plurality of (two or more) projections 12 are formed on the substrate 11. Alternatively, only one projection 12 may be formed on the substrate 11. The hollow needle body 10 is preferably configured such that the plurality of projections 12 are formed and arrayed on the substrate 11. A medicine dose per puncture is expected to increase by forming the plurality of projections 12. In the case where a dose is prescribed, the medicine can be administered in a shorter time by forming the plurality of projections 12. Examples of the array pattern include a grid, concentric, close-packed, and random array patterns when viewed from a direction perpendicular to the first surface 11S of the substrate 11. The projection 12 of the hollow needle body 10 preferably has a height L in the range of 0.3 mm to 2.0 mm, inclusive.

The projection 12 preferably has a conic solid shape, a cross-sectional area of which is reduced toward the distal end. FIG. 1 illustrates the case where the projection 12 is formed in a conic solid shape such as a cone and a pyramid. Alternatively, as the shape of the projection 12, it is also possible to select a pencil shape by combining a conic solid shape with a columnar shape such as a cylinder and a prism (a body part has a columnar shape and a distal end part has a conical shape). A constriction or a step may be appropriately formed in a side wall of the projection 12. In FIG. 1, an outlet of the through hole 13 is formed at the tip of the projection 12. Alternatively, the outlet of the through hole 13 may be formed in a side surface of the projection 12.

A material having biocompatibility is desirable as a material for the hollow needle body 10. Examples of the material having biocompatibility include: metals such as stainless steel, titanium, manganese, and silicon; ceramics such as alumina, zirconia, silicon carbide, and silicon nitride; and resins such as medical silicone, polylactic acid, polyglycolic acid, and polycarbonate.

The hollow needle body 10 can be fabricated using various known techniques. For example, in the case where a resin is used as the material, the hollow needle body 10 can be fabricated by forming the substrate 11 and the plurality of projections 12 by means of a forming technique such as injection, extrusion, imprinting, hot embossing, and casting, followed by forming the through hole 13 in each of the projections 12 by means of a micro drill, a laser or the like.

<Puncture Injection Instrument>

With reference to FIGS. 2 to 5, a configuration of the puncture injection instrument according to the first embodiment will be described.

Figure 2:
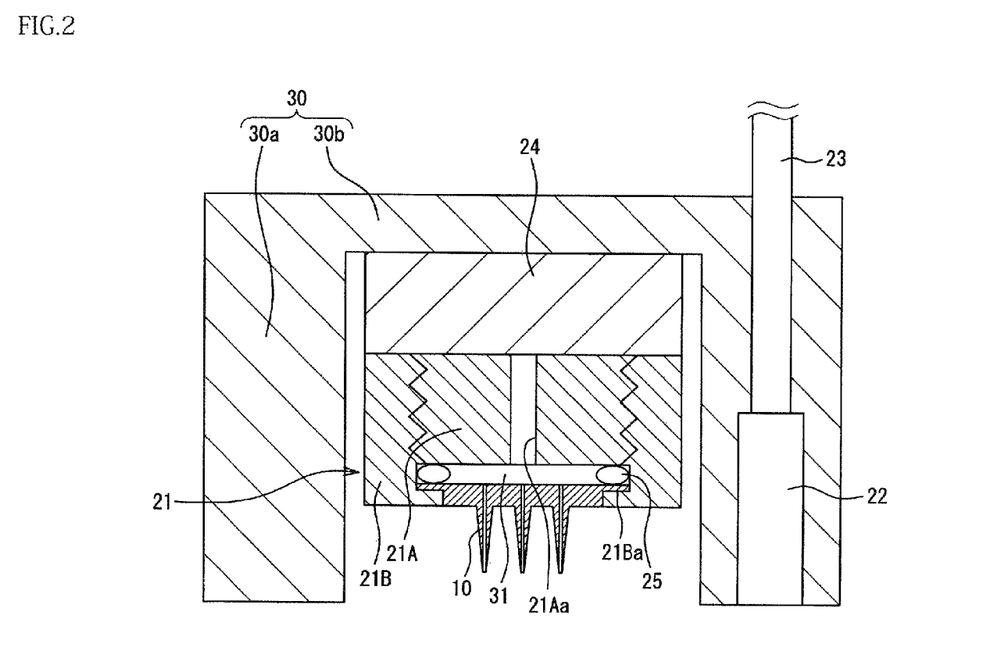
FIG. 2 is a schematic cross-sectional view illustrating a puncture injection instrument according to the first embodiment of the present invention.

As illustrated in FIG. 2, the puncture injection instrument of the first embodiment includes the hollow needle body 10, a holder 21, and an ultrasound probe 22. The puncture injection instrument also includes a liquid-tight member 25 as necessary.

The holder 21 has a structure such that the hollow needle body 10 can be mounted thereto. As a structure for mounting the hollow needle body 10 to the holder 21, a known detachable structure can be employed. Examples of the known detachable structure include a fitting type mounting structure provided by a combination of a female part and a male part, a mounting structure using a screw, a mounting structure provided by a snap fit, a mounting structure provided by an independent fixing screw, and a mounting structure provided by a combination of an independent fixing screw and a pressing plate.

Figure 3:
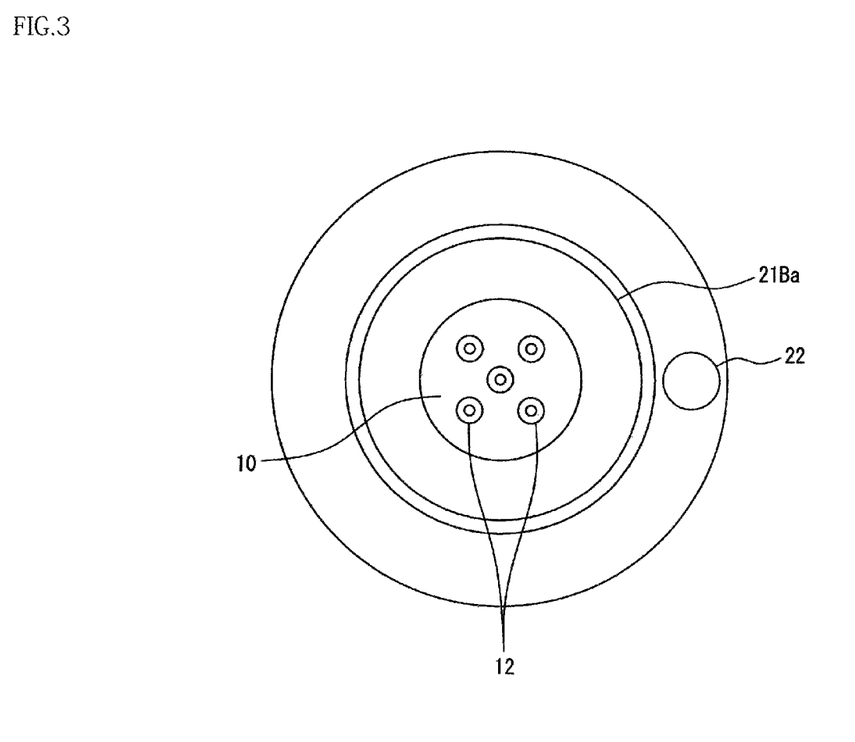
FIG. 3 is a schematic bottom view illustrating the puncture injection instrument according to the first embodiment of the present invention.

FIGS. 2 and 3 illustrate the case where the holder 21 includes a columnar part 21A and a cylindrical part 21B that are coaxially arranged, and has such a structure that the columnar part 21A can be threadably mounted to a radially-inward surface of the cylindrical part 21B. Materials for the columnar part 21A and the cylindrical part 21B are not particularly limited. For example, various metals, resins, ceramics, and glass can be used as the materials. It is important to select the material in consideration of drug resistance, processability, strength, and cost or the like. The cylindrical part 21B is formed to have an inner diameter somewhat larger than a diameter of the substrate 11 of the hollow needle body 10. At a lower end part of the cylindrical part 21B, an inward flange 21Ba for receiving the substrate 11 from below is formed.

The hollow needle body 10 is inserted from an upper end opening side of the cylindrical part 21B, an outer peripheral lower surface of the hollow needle body 10 is supported by an upper surface of the inward flange 21Ba, and then the columnar part 21A is mounted. In this case, the hollow needle body 10 is inserted such that the first surface 11S, that is, the surface on which the plurality of projections 12 are formed, is directed downward. The liquid-tight member 25 is arranged between the lower end surface of the columnar part 21A and the upper surface of the substrate 11 to form a chamber 31 therebetween. A medicine injection channel 21Aa extending in a vertical direction is formed in the columnar part 21A to inject medicine. The medicine injection channel 21Aa guides a medicine to an upper surface side of the substrate 11, that is, to the second surface 11T side so as to be injected into the skin through the projections 12.

An operation unit 24 is mounted to an upper end part of the holder 21. The operation unit 24 includes an energizing force generation source for causing the projections 12 of the hollow needle body 10 to puncture a puncture object, and a mechanism for delivering a liquid to the hollow needle body 10. Examples of the energizing force generation source include a compression spring, a tension spring, an elastic material, a drive mechanism using a magnet, a compressed gas drive mechanism including compressed air, and an electric drive mechanism. The operation unit 24 may further include a switch mechanism for operating such sources. Examples of the switch mechanism include: a known latching mechanism that stops movement of a drive member by resisting against an energizing force from an energizing force generation source, not illustrated, (mechanism to release the energizing force by releasing a latch); a trigger mechanism (mechanism to release the energizing force by pulling a trigger); a pusher mechanism (mechanism to release the energizing force by pressing a pusher or a push button); and a manual/electromagnetically driven on-off valve capable of selectively supplying compressed gas from a compressed gas supply source including compressed air to a drive member (not illustrated).

As illustrated in FIG. 2, a bottomed outer cylindrical body 30 is arranged coaxially with the holder 21 so as to cover, from above, the holder 21 including the outer peripheral side surface thereof. The outer cylindrical body 30 is configured so that an upper surface disk part 30b and a thick outer cylinder part 30a are integrated with each other. The holder 21 is attached to a lower surface of the upper surface disk part 30b via the operation unit 24.

FIG. 2 illustrates the case where the outer cylindrical body 30 and the operation unit 24 are separately formed. Alternatively, the outer cylindrical body 30 and the operation unit 24 may be collectively formed.

The ultrasound probe 22 is attached to a lower end part of the outer cylinder part 30a. Thus, the ultrasound probe 22 is supported by the holder 21 via the outer cylinder part 30a. The ultrasound probe 22 is arranged so as to be capable of detecting an object in a direction along a protruding direction of the projections 12. The ultrasound probe 22 is coupled to an ultrasound sensor body, not illustrated, by wiring 23, and sends detected information to the ultrasound sensor body. For example, the ultrasound sensor body may have a display unit to display the received information. The ultrasound sensor body may specifically include an ultrasound thickness gauge, a power source, and an oscilloscope or the like for general purposes.

The ultrasound probe 22 includes a transmission function and a reception function for ultrasound. Ultrasound transmitted from the ultrasound probe 22 can generate various reflected waves according to differences in acoustic impedance of a living tissue within a living body of a puncture object. Since these reflected waves can be detected by the ultrasound probe 22 as electrical signals, it is possible to measure, for example, the thickness of skin of the puncture object and a site in which a blood vessel exists through analysis of these reflected waves. The first embodiment shows an example of using a reflection type ultrasound probe 22, but other known ultrasound probes may be used.

As illustrated in FIG. 2, the ultrasound probe 22 of the first embodiment has such a structure that the ultrasound probe 22 is incorporated in the outer cylindrical body 30 located on an outer peripheral side of the holder 21. As a structure for mounting the ultrasound probe 22 to the outer cylindrical body 30, a known mounting structure can be employed. Examples of such a known mounting structure include a mounting structure provided by a combination of a female screw and a male screw, a mounting structure provided by a snap fit, a mounting structure provided by an independent fixing screw, a mounting structure provided by a combination of an independent fixing screw and a pressing plate, and a mounting structure provided by a sealing material such as an adhesive.

The ultrasound probe 22 is preferably arranged outside a forming region of the projections 12 of the hollow needle body 10 mounted to the holder 21. More preferably, the ultrasound probe 22 is arranged so that a distal end of the ultrasound probe 22 and a lower end surface of the holder 21 (first surface 11S of the substrate 11) form a horizontal plane (flush plane). When a distal end surface of the ultrasound probe 22 is arranged receding from the lower surface of the substrate 11, a layer of air is created at the time of contact with the skin of a puncture object, whereby transmission of ultrasound is hindered. The distal end surface of the ultrasound probe 22 may be designed to protrude from the plane flush with the lower surface of the substrate 11 in accordance with a puncture amount of the projection 12. Alternatively, the ultrasound probe 22 may be designed to be movable back and forth relative to the skin, being energized by a mechanism such as a spring and a screw.

In the frequency range of the ultrasound probe 22, the center frequency is preferably higher than 15 MHz and lower than 80 MHz. A low-frequency region of 15 MHz or less is not suitable for observation of the thickness of the skin due to the low resolution. A high-frequency region of 80 MHz or more causes such a problem that only a narrow region with a thickness of not more than the thickness of the skin can be observed due to the shallow measurement depth.

Figure 4:
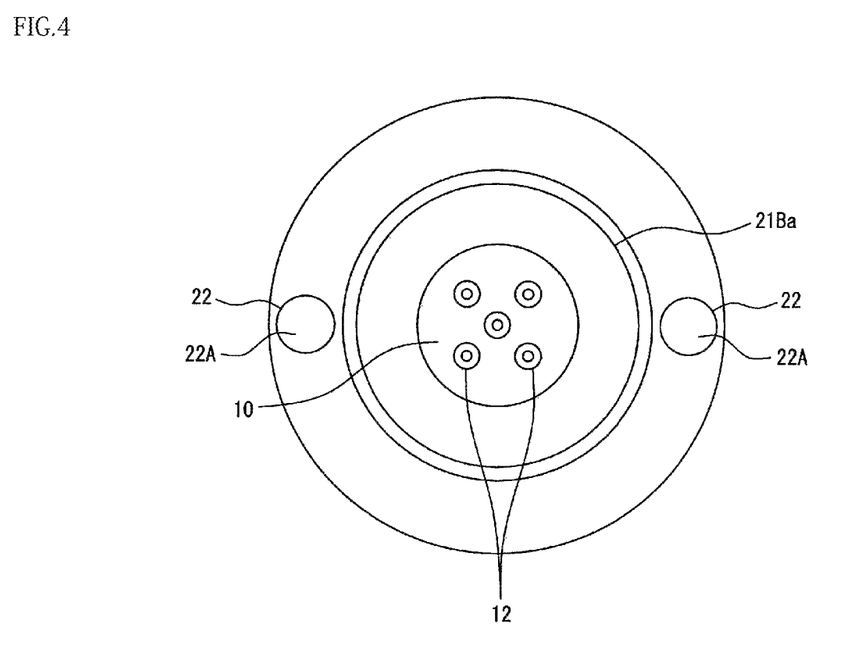
FIG. 4 is a schematic bottom view illustrating a puncture injection instrument according to a modification of the first embodiment.

The ultrasound probe 22 may include an acoustic lens 22A as illustrated in FIG. 4. When the acoustic lens 22A is included, ultrasound can be converged by use thereof to improve the resolution performance, or ultrasound can be diffused to obtain data of a broader region. Various resin materials can be used for the acoustic lens 22A. More specifically, silicone rubber or the like may be used.

FIGS. 2 and 3 illustrate the case where only one ultrasound probe 22 is mounted. Alternatively, a plurality of (two or more) ultrasound probes 22 may be attached as illustrated in FIG. 4. When a plurality of ultrasound probes 22 are combined and used, the electrical signals that can be noises are not selected. When the plurality of ultrasound probes 22 is operated in sequence, the observation plane can be scanned. The pieces of scan data may be combined and displayed, for two-dimensional mapping.

Materials for the components configuring the puncture injection instrument of the first embodiment are not particularly limited. For example, the material for the holder 21 may include plastic, glass, ceramics, metal, an elastomer, or the like. In particular, examples of the plastic include polyethylene, polypropylene, polystyrene, polyamide, polycarbonate, a cyclic polyolefin, acryl, a urethane resin, an epoxy resin, and the like. As the ultrasound probe 22, for example, various ultrasound probes that are widely distributed can be appropriately employed.

As the liquid-tight member 25, an annular member that is parallel to an inner peripheral surface of the cylindrical part 21B of the holder 21 is preferable. FIG. 2 illustrates the case where the liquid-tight member 25 is formed in an annular shape such as an O-ring and a gasket. Materials for the liquid-tight member 25 are not particularly limited. For example, a material for the liquid-tight member 25 can be appropriately selected in consideration of chemical resistance and water resistance. The liquid-tight member 25 surrounds all the openings of the plurality of through holes 13 opened in the second surface 11T of the hollow needle body 10.

Figure 5:
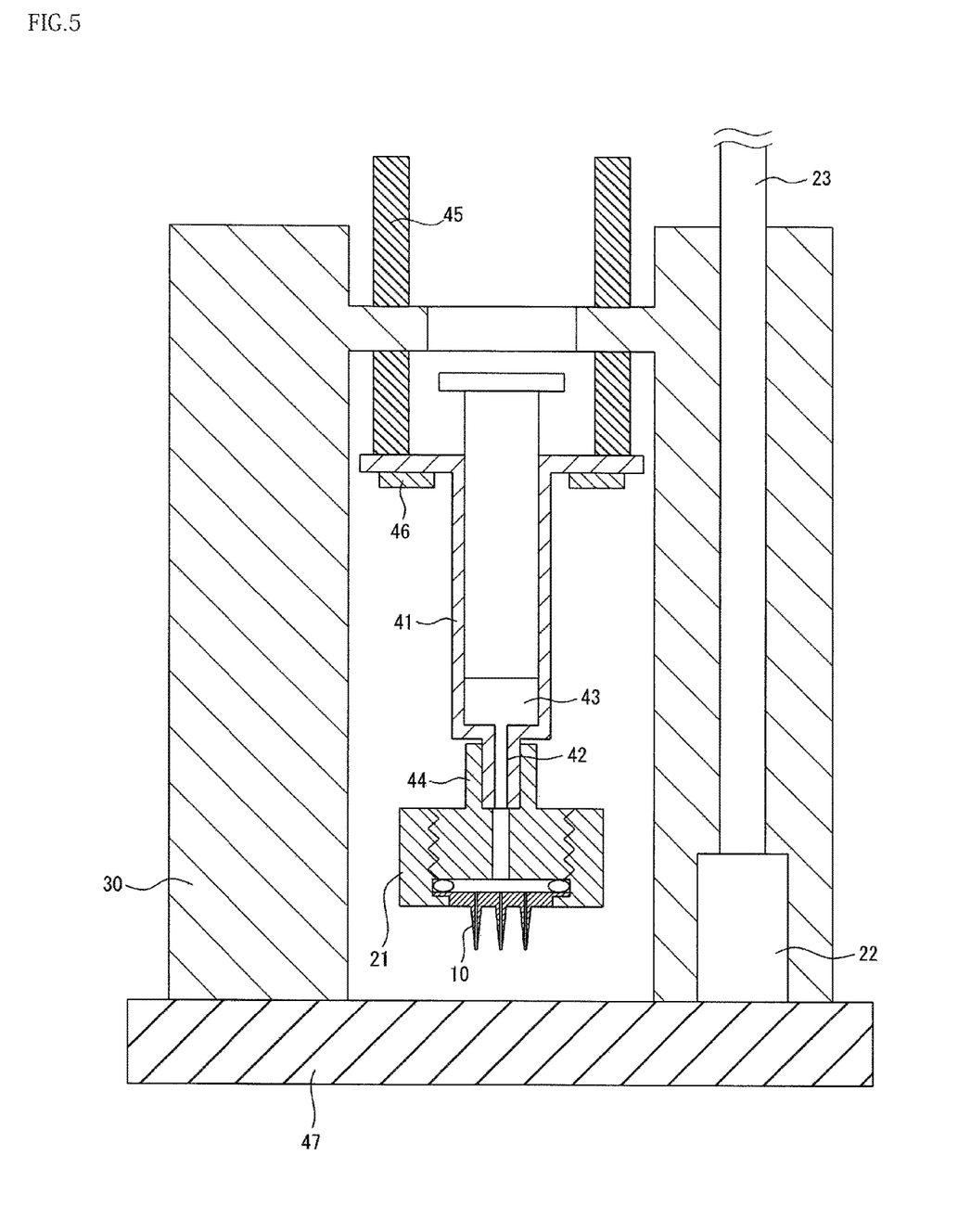
FIG. 5 is a schematic cross-sectional view illustrating the puncture injection instrument according to the first embodiment of the present invention combined with an injector.

The puncture injection instrument of the first embodiment may be used in combination with an injector 41 as illustrated in FIG. 5. In this case, in the cylindrical part 21B of the holder 21, for example, an opening is provided in a surface opposite to a surface that is in contact with the liquid-tight member 25. The opening is provided with a fitting part 44 for mounting an injection cylinder (syringe) of the injector 41. The holder 21 and the injector 41 are coupled to each other through the fitting part 44. Examples of the shape of the fitting part 44 include a tapered shape conforming to a luer lock standard.

In the injection cylinder of the injector 41, a desired amount of intracorporeal injection liquid 43 (e.g., a medicinal solution or a vaccine to be injected into an intradermal layer of an animal as well as a human) may be sucked and retained for use via a through hole of an injection needle attachment projection 42. The injector 41 for a subcutaneous injection is easily available at a moderate price. The injection cylinder of the injector 41 for the subcutaneous injection is substantially transparent so that the amount of the intracorporeal injection liquid 43 retained inside can be visually checked from outside. Moreover, a scale clearly indicating the above-mentioned amount is provided on the outer surface of the injection cylinder. Therefore, the amount of the intracorporeal injection liquid 43 can be easily and precisely changed.

In FIG. 5, the outer cylindrical body 30 is provided with an energizing force generation source 45 for causing the projections 12 of the hollow needle body 10 to puncture a puncture object. Examples of the energizing force generation source 45 include a compression spring, a tension spring, an elastic material, a drive mechanism using a magnet, a compressed gas drive mechanism including compressed air, and an electric drive mechanism. A switch mechanism 46 for operating them may further be included. Examples of the switch mechanism 46 include: a known latching mechanism that stops movement of a drive member by resisting against an energizing force from an energizing force generation source, not illustrated, (mechanism to release the energizing force by releasing a latch), not illustrated; a trigger mechanism (mechanism to release the energizing force by pulling a trigger); a pusher mechanism (mechanism to release the energizing force by pressing a pusher or a push button); and a manual/electromagnetically driven on-off valve capable of selectively supplying compressed gas from a compressed gas supply source including compressed air to a drive member (not illustrated).

A portion that is in contact with the intracorporeal injection liquid 43 needs to be covered with or formed of a substance that does not denature the intracorporeal injection liquid 43 and is not denatured by the intracorporeal injection liquid 43.

In this regard, in FIG. 5, the injector 41 and the energizing force generation source 45 constitute the operation unit 24.

At the time of using the puncture injection instrument of the first embodiment, the ultrasound probe 22 may be used with a polymer gel being applied thereto. The applied polymer gel can suppress creation of an air layer that inhibits transmission of ultrasound, whereby more accurate data can be obtained. The polymer gel may be a medical polymer gel that is widely distributed, and the polymer gel is not particularly limited.

The present inventor has confirmed that the conditions for puncturing the skin depend on the thickness of the skin and the presence/absence of blood vessels under the skin. Specifically, in some cases, the length of the needle body exceeds the thickness of the skin in a thin-skin region, resulting in subcutaneous administration, or stretchability of the skin is poor in a thick-skin region, resulting in high injection resistance. Therefore, it has been found to be effective that a puncture injection position is determined after the skin thickness and adjacent tissue information are obtained, whereby the present application has been made.

Figure 6A:
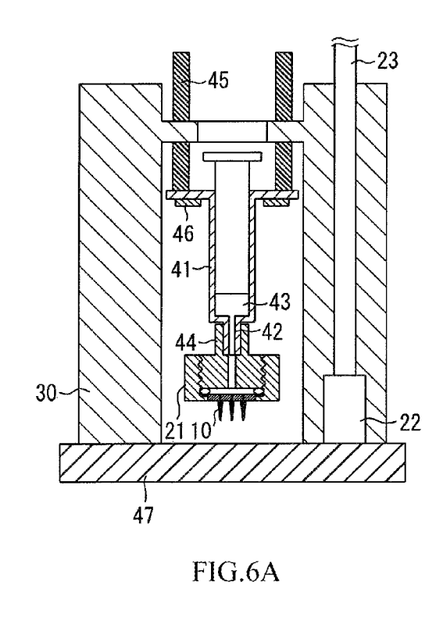
FIGS. 6A-6C are a set of schematic cross-sectional views illustrating a method of using the puncture injection instrument according to the first embodiment of the present invention.
Figure 6B:
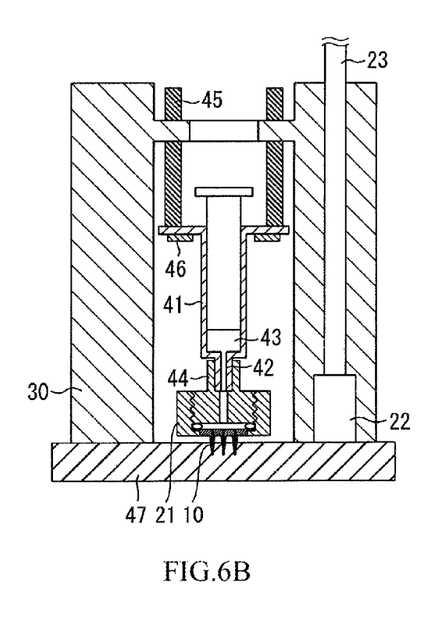
Figure 6C:
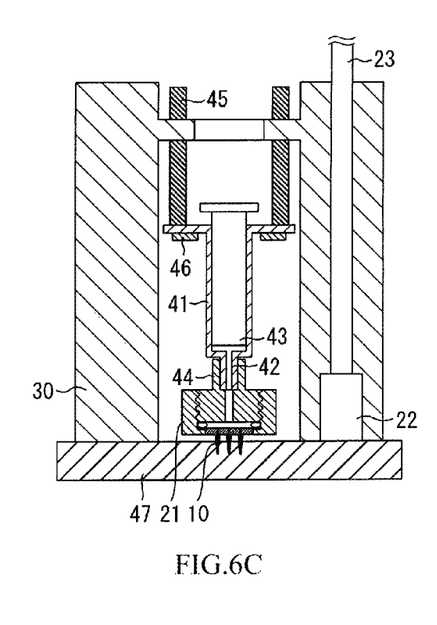

A method of using the puncture injection instrument of the first embodiment will be described with reference to FIGS. 6A-6C. A user of the puncture injection instrument of the first embodiment determines an individual or a spot (site) to be subjected to a puncture injection after obtaining information such as the thickness of the skin of a puncture object 47 using the ultrasound probe 22 before puncture (FIG. 6A). Then, the determined individual or spot (site) is punctured by the projections 12 of the hollow needle body 10 (FIG. 6B). After that, the intracorporeal injection liquid 43 is injected into the determined individual or spot (site) from the projections 12 of the hollow needle body 10 (FIG. 6C).

The puncture injection instrument of the first embodiment may include a lamp. The lamp is connected to the ultrasound sensor body (not illustrated) or the ultrasound probe 22. The lamp can be switched between lit and unlit states in accordance with detected information (an electrical signal) set in advance. The lamp has such a mechanism that an electrical signal of the puncture object 47 is obtained using the ultrasound probe 22 and the lamp is turned on when the electrical signal falls in a proper range set in advance. The user of the puncture injection instrument of the first embodiment moves the puncture injection instrument on the surface of the puncture object 47, and when the electrical signal falls in the proper range set in advance and switch on of the lamp is confirmed, the puncture object 47 is subjected to puncture injection by the projections 12 of the hollow needle body 10. The lamp is used in this way, whereby an appropriate spot (site) on the puncture object 47 can be searched for and the puncture injection can be easily performed at the appropriate spot (site). In the above-mentioned usage mode, the lamp is preferably provided on the holder 21 or the like in terms of visibility for the user of the puncture injection instrument.

The lamp can be switched not only by switching between lit and unlit states but also by the change of color (e.g., red and blue).

In addition to the above-mentioned mode, introduction may be performed using various operation assisting instruments or supply assisting devices for the intracorporeal injection liquid 43. Such an operation assisting instrument or a supply assisting device can be detachably fixed to the holder 21, the ultrasound probe 22, a housing of the injector 41, or an outer surface of a plunger of the injector 41 by a known fixing means including, for example, a fixing screw and a clip, not illustrated.

Example

Hereinafter, an example of the puncture injection instrument of the first embodiment will be described.

The following operation assisting instrument for puncture injection as illustrated in FIG. 5 was prepared.

The hollow needle body 10, the holder 21 for holding the hollow needle body 10, and the 20 MHz ultrasound probe 22 were prepared. The hollow needle body 10 included nine projections 12, each being in a conical shape with a height of 1.3 mm. The hollow needle body 10 was made of polycarbonate and had an outer diameter of 10 mm. The holder 21 was made of polycarbonate. The ultrasound probe 22 was fixed within a housing made of polycarbonate. The hollow needle body 10 and the holder 21 were fixed by a mechanism formed of a male screw and a female screw. The holder 21 included a drive mechanism that used spring power.

As a puncture object, a skin of an eight-week-old Wistar rat and a skin of a twenty-week-old Wistar rat were prepared. The hair was removed by a clipper. An ultrasound gel (SOUNDSAFE: manufactured by DAKOTA JAPAN Inc.) was applied to the ultrasound probe 22. After that, the thickness of each skin was measured by means of ultrasound through an ultrasound thickness gauge (PVX: manufactured by DAKOTA JAPAN Inc.), with the operation assisting instrument for puncture injection being in contact with the skin. Through the measurement it was confirmed that the skin of the eight-week-old Wistar rat had a region where the thickness was of the order of 0.8 mm, and the skin of the twenty-week-old Wistar rat had a region where the thickness was of the order of 1.3 mm.

Saline dyed blue was prepared as the intracorporeal injection liquid 43. The skin of the eight-week-old Wistar rat was punctured by the hollow needle body 10 at a puncture speed of 0.2 m/s. After the puncture became stable, a piston of the injector 41 was pushed, whereby 50 µl of blue-dyed saline was injected into the skin. After the injection, the skin was observed with transmitted light shed from behind. As a result, it was confirmed that the saline did not intradermally remain in the skin, but subcutaneously flowed into the skin, and expanded into a circular shape having a diameter of about 3 cm.

Next, the skin of the twenty-week-old Wistar rat was punctured by the hollow needle body 10 at a puncture speed of 0.2 m/s. After the puncture became stable, the piston of the injector 41 was pushed, whereby the blue-dyed saline was injected into the skin. After the injection, the skin was observed with transmitted light shed from behind. As a result, leakage of the injected saline (intracorporeal injection liquid 43) was not confirmed on the surface of the skin, and it was confirmed that the saline was intradermally injected into a region of about 1 cm in diameter.

Advantageous Effects of First Embodiment

The first embodiment of the invention has the following effects.

(1) The puncture injection instrument according to the first embodiment includes: the hollow needle body 10 having the plurality of projections 12 on the first surface 11S of the substrate 11, with each of the projections 12 being formed with the through hole 13 penetrating from the distal end side of the projection 12 to the second surface 11T of the substrate 11; and the ultrasound probe 22. The ultrasound probe 22 is arranged outside a region in which the plurality of projections 12 are formed.

With this configuration, by using the ultrasound probe 22, information such as the thickness of skin can be obtained before puncture of the projection 12 (hollow needle body 10).

Consequently, it is possible to grasp in advance, for example, an individual or a site having extremely thin skin, an individual or a site having thick skin, or a site in which blood vessels exist, and perform a puncture while avoiding these sites. As a result, a medicine or the like is reliably intradermally administered into the skin without fail, while the medicine is prevented from leaking to the surface of the skin or from subcutaneously leaking in the skin.

(2) The puncture injection instrument according to the first embodiment includes the holder 21 configured to support the hollow needle body 10, the holder 21 having the medicine injection channel 21Aa configured to guide a medicine injected through the projections 12 to the second surface 11T side of the substrate 11. The ultrasound probe 22 is supported by the holder 21.

With this configuration, information such as the thickness of the skin can be acquired in the vicinity of a puncture-conducted site.

(3) The puncture injection instrument according to the first embodiment is configured such that a frequency range of the ultrasound probe 22 has a center frequency higher than 15 MHz and lower than 80 MHz.

With this configuration, information such as the thickness of the skin can be observed with a more suitable resolution or the like.

(4) The puncture injection instrument according to the first embodiment includes two or more ultrasound probes 22.

With this configuration, electrical signals that can be noises are not selected.

(5) The puncture injection instrument according to the first embodiment is configured such that the ultrasound probe 22 includes the acoustic lens 22A.

With this configuration, ultrasound can be converged to improve resolution performance, or ultrasound can be diffused to obtain data of a wider region.

(6) The puncture injection instrument according to the first embodiment is configured such that the hollow needle body 10 is made of a material having biocompatibility.

With this configuration, if the projection 12 is broken and remains within the living body, the projections 12 do not adversely affect the living body.

Second Embodiment

A second embodiment of the present invention will be described with reference to FIGS. 7 to 10B.

Figure 7:
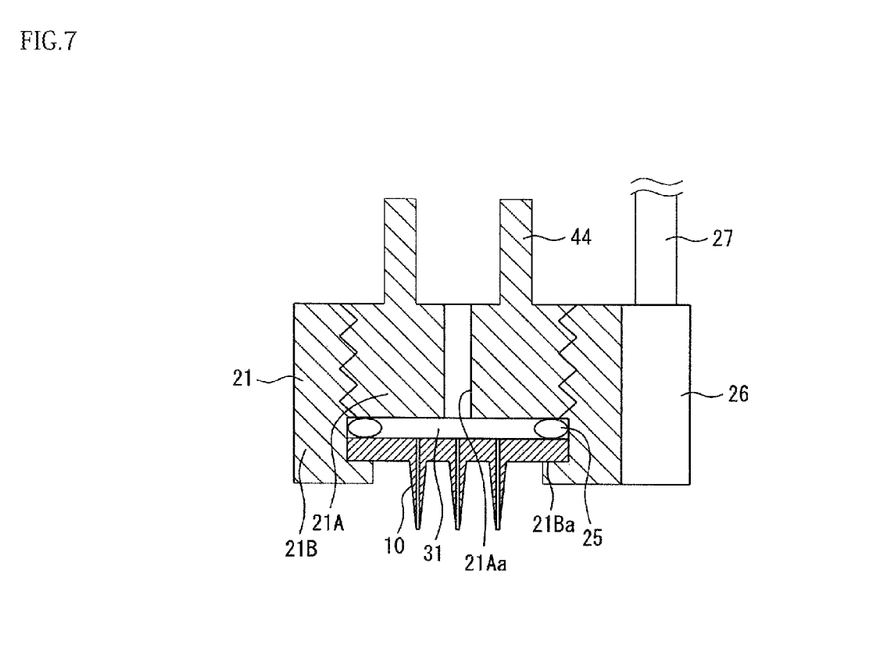
FIG. 7 is a schematic cross-sectional view illustrating a hollow needle body according to a second embodiment of the present invention.

As illustrated in FIG. 7, a puncture injection instrument of the second embodiment is different from that of the first embodiment in that an optical coherence tomography (OCT) probe 26, in place of the ultrasound probe 22, is mounted to a side surface part of the cylindrical part 21B of the holder 21.

Figure 8:
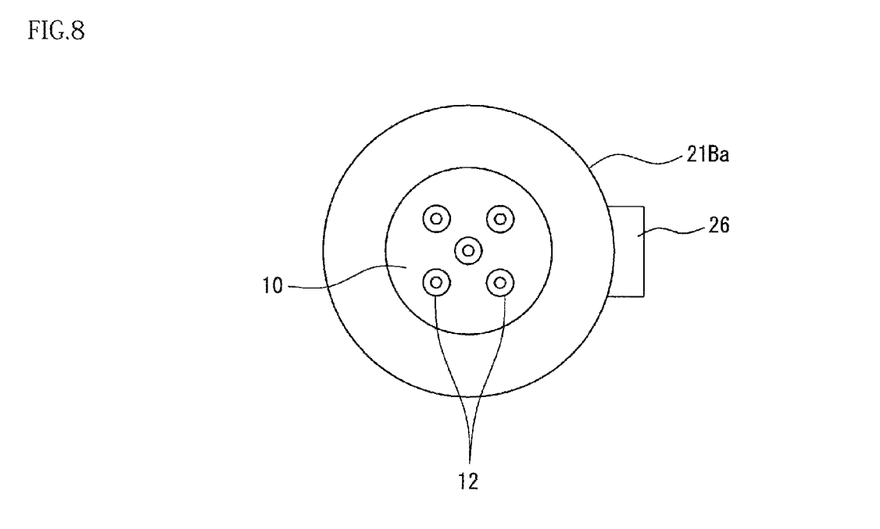
FIG. 8 is a schematic bottom view illustrating a puncture injection instrument according to the second embodiment of the present invention.

As illustrated in FIGS. 7 and 8, the optical coherence tomography probe 26 is attached to an outer peripheral surface of the holder 21. Thus, the optical coherence tomography probe 26 is supported by the holder 21. The optical coherence tomography probe 26 is arranged so as to be capable of detecting an object in a direction along a protruding direction of the projections 12. The optical coherence tomography probe 26 is coupled to an optical coherence tomography sensor body, not illustrated, by wiring 27, and sends detected information to the optical coherence tomography sensor body. For example, the optical coherence tomography sensor body may have a display unit so as to be capable of displaying received information. The optical coherence tomography sensor body may specifically include a power source and an oscilloscope or the like for general purposes.

The optical coherence tomography probe 26 includes functions of emitting and receiving light (near-infrared light) of low temporal coherence. Near-infrared light emitted from the optical coherence tomography probe 26 can generate various reflected light beams depending on a living tissue within a living body of a puncture object. Since these reflected light beams can be detected by the optical coherence tomography probe 26 as electrical signals, the thickness of the skin of the puncture object and the site in which blood vessels exist, for example, can be measured by analyzing the coherence state of the reflected light beams and the emitted light (reference light).

It is important to select as small and light an optical coherence tomography probe 26 as possible in order not to reduce operability of the puncture injection instrument.

Figure 9:
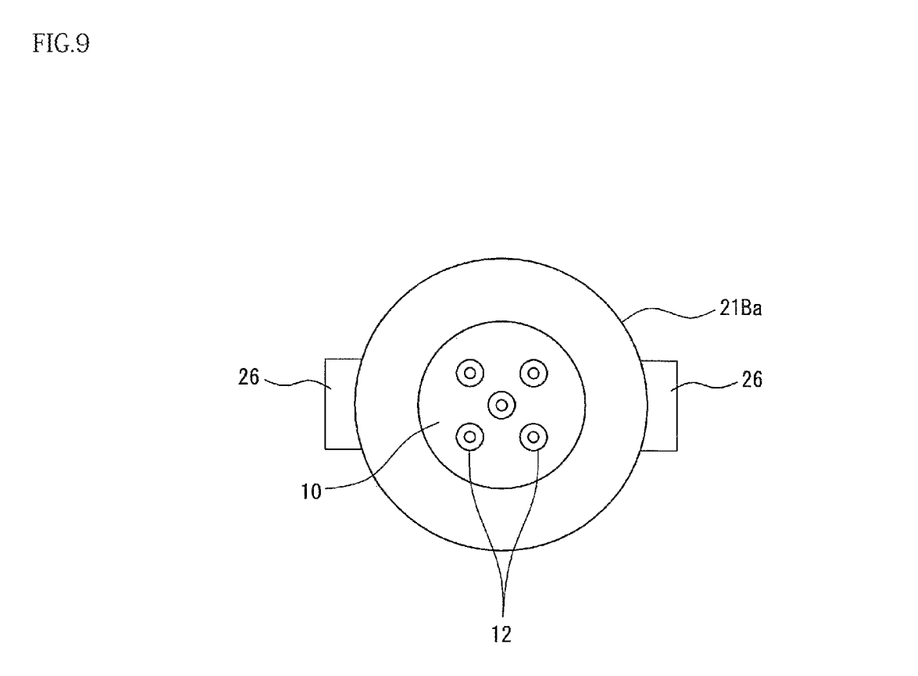
FIG. 9 is a schematic bottom view illustrating a puncture injection instrument according to a modification of the second embodiment.

FIG. 7 illustrates the case where only a single optical coherence tomography probe 26 is mounted. Alternatively, as illustrated in FIG. 9, a plurality of (two or more) optical coherence tomography probes 26 may be mounted. When the plurality of optical coherence tomography probes 26 are combined and used, electrical signals that can be noises are not selected. When the plurality of optical coherence tomography probes 26 are operated in sequence, the observation plane can be scanned. The pieces of scan data may be combined and displayed, for two-dimensional mapping.

The rest of the configuration is the same as that of the first embodiment.

Figure 10A:
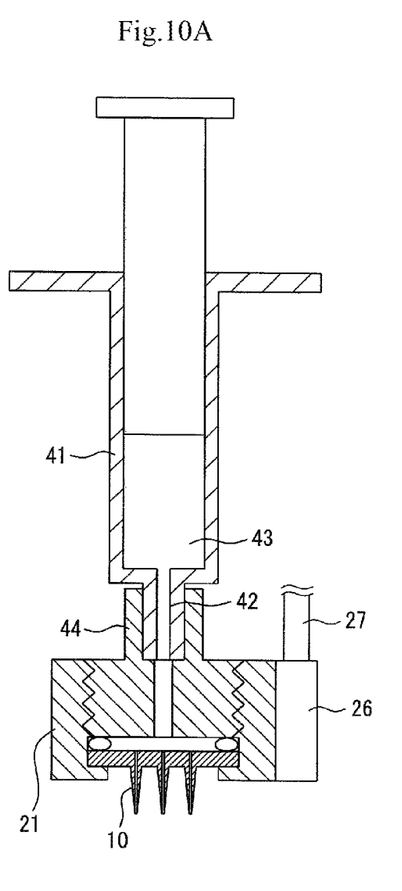
FIGS. 10A and 10B are a set of schematic cross-sectional views illustrating the puncture injection instrument according to the second embodiment of the present invention combined with an injector.
Figure 10B:
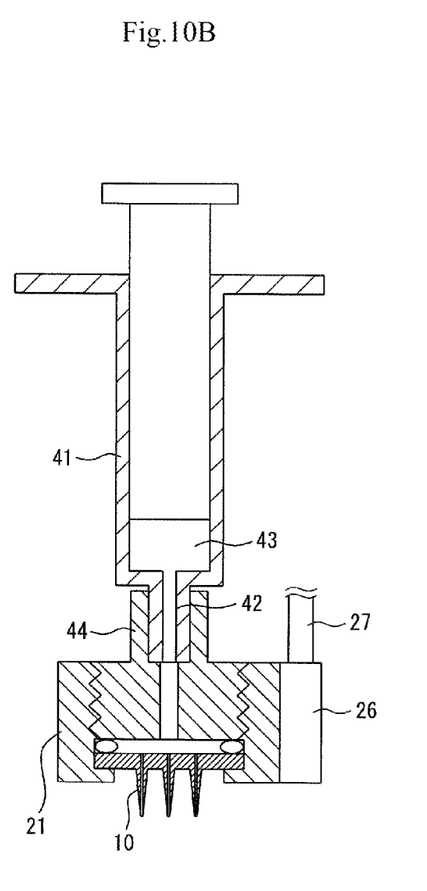

FIGS. 7 and 10B illustrate the case where the upper surface of the inward flange 21Ba is flush with the lower surface of the substrate 11 (first surface 11S), that is, the lower surface of the substrate 11 (first surface 11S) is receding upward by the thickness of the inward flange 21Ba. In this case, it is important to determine the length of the projections 12 in consideration of the thickness of the inward flange 21Ba.

The puncture injection instrument of the second embodiment may be used in combination with the injector 41 as illustrated in FIGS. 10A and 10B. As illustrated in FIG. 10A, the injection cylinder (syringe) of the injector 41 is preliminarily filled with the intracorporeal injection liquid 43 that is to be administered into skin. Next, the puncture injection instrument to which the injection cylinder (syringe) of the injector 41 has been connected is arranged at a position suitably distanced from the skin (not illustrated), and the thickness of the skin or the like is measured by the optical coherence tomography probe 26. Then, puncture conditions for allowing the projections 12 of the hollow needle body 10 to fall within the skin are selected based on information such as the measured thickness of the skin, and a relationship of the preliminarily studied puncture conditions with puncture depth. The puncture conditions include, for example, a puncture load, a puncture speed, and an injection pressure of the hollow needle body 10. The puncture injection instrument is then pressed against the skin under the selected puncture conditions. Although a method of pressing the puncture injection instrument against the skin is not particularly limited, an assisting instrument may be used for pressing with accuracy. Subsequently, as illustrated in FIG. 10B, the piston of the injector 41 is pushed by hand whereby the intracorporeal injection liquid 43 is administered into the skin.

Example

Hereinafter, an example of the puncture injection instrument of the second embodiment will be described.

The hollow needle body 10 made of polycarbonate was manufactured by injection. The hollow needle body 10 was provided with five projections 12, each being in a conical shape with a height of 2 mm, and the substrate 11 with a thickness of 500 μm and an outer diameter of 10 mm. Then, the through hole 13 with a diameter of 50 μm as formed in each of the projections 12 by laser processing.

The cylindrical part 21B including the inward flange 21Ba with a thickness of 0.3 mm was prepared. The cylindrical part 21B was made of stainless steel with an inner diameter of 10.4 mm, an outer diameter of 14 mm, and a thickness of 15 mm. The columnar part 21A made of stainless steel was further prepared. The liquid-tight member 25 with a wire diameter of 1 mm was also prepared. The columnar part 21A and the cylindrical part 21B were fit with each other by thread grooves provided in respective side surfaces.

The optical coherence tomography probe 26 with a thickness of 10 mm was mounted to an outer peripheral surface of the cylindrical part 21B using near-infrared light with a wave length of 1300 nm. The puncture injection instrument was obtained in this way.

As a puncture object, a skin of an eight-week-old Wistar rat and a skin of a twenty-week-old Wistar rat were prepared. The hair was removed by a clipper. The thickness of each skin was measured by means of the optical coherence tomography probe 26, with the operation assisting instrument for a puncture injection being spaced away from the skin by about 10 mm. Through the measurement it was confirmed that the skin of the eight-week-old Wistar rat had a region where the thickness was of the order of 0.8 mm, and the skin of the twenty-week-old Wistar rat had a region where the thickness was of the order of 1.3 mm.

Effects of Second Embodiment

The second embodiment of the invention has the following advantageous effects.

(1) The puncture injection instrument according to the second embodiment includes: the hollow needle body 10 having the plurality of projections 12 on the first surface 11S of the substrate 11, with each of the projections 12 being formed with the through hole 13 penetrating from the distal end side of the projection 12 to the second surface 11T of the substrate 11; and the optical coherence tomography probe 26. The optical coherence tomography probe 26 is arranged outside a region in which the plurality of projections 12 are formed.

With this configuration, by using the optical coherence tomography probe 26, information such as the thickness of the skin can be obtained before puncture by the projections 12 (hollow needle body 10).

(2) The puncture injection instrument according to the second embodiment includes the holder 21 configured to support the hollow needle body 10, the holder 21 having the medicine injection channel 21Aa configured to guide a medicine to be injected through the projections 12 to the second surface 11T side of the substrate 11. The optical coherence tomography probe 26 is supported by the holder 21.

With this configuration, information such as the thickness of the skin can be acquired in the vicinity of a puncture-conducted site.

(3) The puncture injection instrument according to the first embodiment includes two or more optical coherence tomography probes 26.

With this configuration, electrical signals that can be noises are not selected.

Several methods have been considered as a method of intradermally administering a medicine using a needle body, examples of which include: a method of applying a medicine to a surface of the skin before or after causing a needle body to puncture the skin; a method of causing a needle body with a medicine applied to its surface in advance or a needle body made of a material containing a medicine to puncture the skin; and a method of causing a hollow needle body, that is a needle body provided with a through hole, to puncture the skin and administering a medicine into the skin by way of the through hole.

Compared with other methods, the administration method using the hollow needle body having a through hole is advantageous in that a liquid dosage form can be utilized and a medicine dose can be easily adjusted in the same way as a conventional subcutaneous injection, but has such a problem that a portion of the medicine is likely to leak to a surface of the skin or under the skin during the administration.

As a measure to prevent liquid leakage, for example, an injection drug delivery device including a needle, a limiter, and a rigid stabilizer has been proposed (refer to Patent Literature 2). Specifically, the limiter controls an insertion depth of the needle, and the rigid stabilizer prevents distortion, compression, or thinning of a tissue in the vicinity of the needle insertion part.

When the device described in Patent Literature 2 is used, however, an optimal insertion depth needs to be estimated in advance in accordance with the thickness of the skin that varies due to an individual difference such as age, race, gender, and constitution.

The present invention can provide a puncture injection instrument for reliably administering a medicine or the like into skin while suppressing leakage of the medicine to a surface of the skin when the medicine is intradermally administered using a hollow needle body.

In order to solve the above-mentioned problems, an aspect of the present invention is characterized in that the instrument includes: a hollow needle body having one or more projections on a first surface of a substrate, each of the projections being formed with a through hole penetrating from a distal end side of the projection to a second surface of the substrate, the second surface being opposite to the first surface; and an ultrasound probe or an optical coherence tomography probe. In the instrument the ultrasound probe or the optical coherence tomography probe is arranged outside a region in which the one or more projections are formed.

According to an aspect of the present invention, by using an ultrasound probe or an optical coherence tomography probe, information such as the thickness of the skin can be obtained before puncture by the projections (hollow needle body).

Thus, it is possible to detect in advance, for example, an individual or a site having an extremely thin skin, an individual or a site having a thick skin, or a site in which blood vessels exist, enabling puncture avoiding these sites. As a result, a medicine or the like can be reliably intradermally administered into the skin without fail, while preventing leakage of the medicine to the surface of the skin or preventing subcutaneous leakage of the medicine in the skin.

The description has so far been provided with reference to a limited number of embodiments, but the scope of rights should not be construed as being limited to these embodiments. Modifications of the embodiments based on the above disclosure should be obvious to a person skilled in the art.

REFERENCE SIGNS LIST 10 hollow needle body
11 substrate
12 projection
13 through hole
21 holder
22 ultrasound probe
26 optical coherence tomography probe
30 outer cylindrical body Obviously, numerous modifications and variations of the present invention are possible in light of the above teachings. It is therefore to be understood that within the scope of the appended claims, the invention may be practiced otherwise than as specifically described herein.

What is claimed is:

1. A puncture injection instrument, comprising:
a hollow needle body comprising a substrate and at least one projection formed on a first surface of the substrate such that the hollow needle body has a through hole penetrating from a distal end of the projection to a second surface of the substrate on an opposite side with respect to the first surface;
a holder detachably supporting the hollow needle body and having an injection channel formed through the holder such that the hollow needle body is mounted on one end of the holder and that the injection channel is connected to discharge liquid to the through hole of the hollow needle body; and
a probe comprising an ultrasound probe or an optical coherence tomography probe and positioned along the hollow needle body in a direction of the projection extending from the substrate such that the probe detects information of a skin to be punctured by the projection of the hollow needle body mounded on the holder and sends the information to a sensor body,
wherein the information of the skin includes at least one of a thickness of the skin and a site of a blood vessel under the skin, and the holder is configured to form a chamber between the second surface of the substrate and an end surface of a portion of the holder such that the chamber is connected to the injection channel of the holder and the through hole of the hollow needle body.

2. The puncture injection instrument of claim 1, wherein the holder is configured to support the probe.

3. The puncture injection instrument of claim 1, wherein the probe comprises an ultrasound probe which has a frequency range in which a center frequency is higher than 15 MHz and lower than 80 MHz.

4. The puncture injection instrument of claim 2, wherein the probe comprises an ultrasound probe which has a frequency range in which a center frequency is higher than 15 MHz and lower than 80 MHz.

5. The puncture injection instrument of claim 1, wherein the probe comprises a plurality of ultrasound probes or optical coherence tomography probes.

6. The puncture injection instrument of claim 2, wherein the probe comprises a plurality of ultrasound probes or optical coherence tomography probes.

7. The puncture injection instrument of claim 3, wherein the probe comprises a plurality of ultrasound probes or optical coherence tomography probes.

8. The puncture injection instrument of claim 4, wherein the probe comprises a plurality of ultrasound probes or optical coherence tomography probes.

9. The puncture injection instrument of claim 1, wherein the probe comprises an ultrasound probe including an acoustic lens.

10. The puncture injection instrument of claim 2, wherein the probe comprises an ultrasound probe including an acoustic lens.

11. The puncture injection instrument of claim 3, wherein the probe comprises an ultrasound probe including an acoustic lens.

12. The puncture injection instrument of claim 4, wherein the probe comprises an ultrasound probe including an acoustic lens.

13. The puncture injection instrument of claim 5, wherein the probe comprises an ultrasound probe including an acoustic lens.

14. The puncture injection instrument of claim 1, wherein the hollow needle body comprises a material having biocompatibility.

15. The puncture injection instrument of claim 1, wherein the holder comprises a cylindrical part configured to accommodate the hollow needle body inside the cylindrical part, and a columnar part configured to be mounted inside the cylindrical part such that the chamber is formed inside the cylindrical part between the second surface of the substrate and an end surface of the columnar part forming the end surface of the portion of the holder.

16. The puncture injection instrument of claim 1, wherein the at least one projection of the hollow needle body comprises a plurality of projections formed on the first surface of the substrate such that each of the projections has the through hole penetrating from a distal end of a respective one of the projections to the second surface of the substrate.

17. The puncture injection instrument of claim 1, further comprising:
a liquid-tight member positioned in the chamber of the holder between the second surface of the substrate and the end surface of the portion of the holder such that the liquid-tight member is surrounding an opening of the through hole on the second surface of the substrate.

18. The puncture injection instrument of claim 1, wherein the hollow needle body has an inward flange, and the holder comprises a cylindrical part configured to accommodate the hollow needle body inside the cylindrical part and engage with the inward flange of the hollow needle body, and a columnar part configured to be mounted inside the cylindrical part such that the first surface of the substrate is positioned at an end of the cylindrical part and that the chamber is formed inside the cylindrical part between the second surface of the substrate and an end surface of the columnar part forming the end surface of the portion of the holder.

19. The puncture injection instrument of claim 1, further comprising:
   a liquid-tight member positioned in the chamber of the holder between the second surface of the substrate and the end surface of the portion of the holder such that the liquid-tight member is surrounding an opening of the through hole on the second surface of the substrate,
   wherein the holder comprises a cylindrical part configured to accommodate the hollow needle body inside the cylindrical part, and a columnar part configured to be mounted inside the cylindrical part such that the chamber is formed inside the cylindrical part between the second surface of the substrate and an end surface of the columnar part forming the end surface of the portion of the holder.

20. The puncture injection instrument of claim 1, further comprising:
   a cylindrical body accommodating the holder and the hollow needle body mounted on the holder inside the cylindrical body, and supporting the probe positioned along the holder in the direction of the projection extending from the substrate.

* * * * *